United States Patent [19]
Brush et al.

[11] Patent Number: 5,556,959
[45] Date of Patent: Sep. 17, 1996

[54] INDOCARBOCYANINE-LINKED PHOSPHORAMIDITES

[75] Inventors: Charles K. Brush, Whitefish Bay; Eric D. Anderson, Oak Creek, both of Wis.

[73] Assignee: Pharmacia P-L Biochemicals Inc., Milwaukee, Wis.

[21] Appl. No.: 265,569

[22] Filed: Jun. 24, 1994

Related U.S. Application Data

[63] Continuation of Ser. No. 7,444, Jan. 22, 1993, abandoned.

[51] Int. Cl.$^6$ ............................. C07H 21/00; C12Q 1/68
[52] U.S. Cl. .............. 536/25.32; 536/241; 536/25.3; 536/25.31; 548/416; 548/455; 435/6
[58] Field of Search ...................... 536/24.1, 25.3, 536/25.31, 25.32; 435/6; 548/416, 455

[56]   References Cited

U.S. PATENT DOCUMENTS 4,981,977  1/1991  Southwick et al. .................. 548/455

FOREIGN PATENT DOCUMENTS 9117169  11/1991  WIPO.

OTHER PUBLICATIONS

Kenten et al. (1992) Clin. Chem. vol. 38(6); 873–879.
Patonay et al. (1991) Analy. Chem. vol. 63(6); 321–326.
Mag et al. (1989) Nuc. Acids Res. vol. 17(15): 5973–5988.
Sekine et al. (1986) J. Am. Chem. Soc. vol. 108: 4581–4586.
Collaborative Research (1978) Semiannual Progress Report No. 2, 6 Jan. 1978–15 Jul. 1978.
Nippon Zeon (1987) JP 62070391.
Schulhof et al., Nucleic Acids Research 15 (1987), pp. 397–416.
Cyanine Dye Labeling Reagents–Carboxymethylindocyanine Succinimidyl Esters, Southwick, et al., *Cytometry*, 11:418–430 (1990).
Synthesis of a Carbocyanine Phosphoramidite and its use in Oligonucleotide Labeling, International Conference on Nucleic Acid Medical Applications, Anderson, et al. (Jan. 15, 1993).
Sensitive Detection of RNAs in Single Cells by Flow Cytometry, *Nucleic Acids Ressearch*, vol. 20, No. 1:83–88, Hong Yu, et al., Dec. 4, 1991.
Ogilvie et al. Proc. Natl. Acad. Sci. USA 85 5764–5768 (1988) Total Chemical Synthesis of a 77–nucleotide–long . . .
Seliger et al. Chem. Ber. 111 3732–3739 (1978) Kinetik der Schutzgruppenabspaulung bei derivaten des . . . .
Dahl et al. Nucleic Acids Research 15 1729–1743 (1987) Mechanistic Studies on the phosphoramidite coupling reaction . . . .

*Primary Examiner*—John L. LeGuyader
*Assistant Examiner*—John S. Brusca
*Attorney, Agent, or Firm*—Quarles & Brady

[57]    ABSTRACT

A chemical compound of the following formula is disclosed

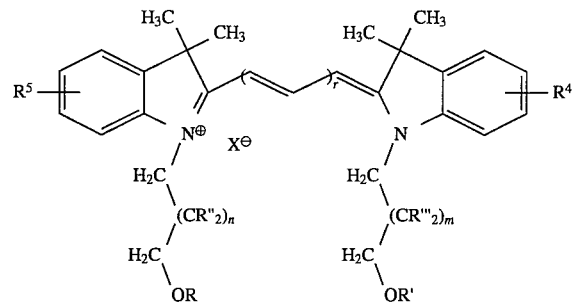

where R is one of H, trityl, 4-0-monomethoxytrityl, 4,4'-O-dimethoxytrityl, or acyl groups and R may be used as a protecting group or is an H; $R^1$ is a phosphoramidite; $R^{11}$ is one of H or lower alkyl groups; $R^{111}$ is one of H or lower alkyl groups; $R^4$ is one of H, lower alkyl, acyl, or $(CH_2)_p COO(CH_2)_q CH_3$ where p is an integer from 0 to 4 and q is an integer from 0 to 4; $R^5$ is one of H, lower alkyl, acyl, or $(CH_2)_p COO(CH_2)_q CH_3$ where p is an integer from 0 to 4 and q is an integer from 0 to 4; n is an integer from 0 to 10; m is an integer from 0 to 10; and r is 1, 2, or 3.

11 Claims, 7 Drawing Sheets

Prior Art

Fig. 1

Scheme 1

$$5'\text{-HO-oligo} \rightarrow \text{(Imidazole)COO-oligo}$$
$$\underline{II} \qquad\qquad\qquad \underline{III}$$

$$\underline{III} + H_2N(CH_2)_3NH_2 \rightarrow NH_2(CH_2)_3NHCOO\text{-oligo}$$
$$\underline{IV}$$

$$\underline{IV} + CCy\text{-}(C=O)\text{-NHS} \rightarrow CCy\text{-CONH}(CH_2)_3NHCOO\text{-oligo}$$
$$\underline{V} \qquad\qquad\qquad\qquad \underline{VI}$$

CCy = Indocarbocyanine

Scheme 2

$$CF_3CONH(CH_2)_6OPam + 5'\text{-HO-oligo} \rightarrow CF_3CONH(CH_2)_6OPO_2\text{-oligo}$$
$$\underline{VII} \qquad\qquad\qquad\qquad\qquad\qquad \underline{VIII}$$

Pam = $P\text{-}(N(CH(CH_3)_2)_2)(OCH_2CH_2CN)$

$$\underline{VIII} + \text{ammonia} \rightarrow NH_2(CH_2)_6OPO_2\text{-oligo}$$
$$\underline{IX}$$

$$\underline{IX} + CCy\text{-}(C=O)\text{-NHS} \rightarrow CCy\text{-CONH}(CH_2)_6OPO_2\text{-oligo}$$
$$\underline{V} \qquad\qquad\qquad\qquad \underline{X}$$

CCy = Indocarbocyanine

Prior Art

Fig. 2

Pam = phosphoramidite
MMTr = monomethoxytrityl

Fig. 3

*XIVa*

*XIVb*

MMTr = monomethoxytrityl

Pam = phosphoramidite

XIX

Fig. 7

INDOCARBOCYANINE-LINKED PHOSPHORAMIDITES

This application is a continuation of application Ser. No. 08/007,444, filed Jan. 22, 1993, abandoned.

FIELD OF THE INVENTION

In general, the present invention relates to indocarbocyanine dyes. Specifically, the present invention relates to the attachment of indocarbocyanine dyes to oligonucleotides.

BACKGROUND

Labelling of Oligonucleotides

Fluorescent, non-radioactive labelling is a highly desirable method for the detection of nucleic acids. For example, this method is useful in automated DNA sequencing, in situ detection of hybridization, detection of PCR products, structural studies, and any of several other applications. In the past, labelling of oligonucleotides has been most conveniently accomplished on an automated synthesizer by introduction of a derivatized deoxyuridine amidite[1] or a linker amidite bearing a protected primary amine[2,3] or thiol.[4] (By "oligonucleotide" we mean an oligomer of DNA, RNA, or modifications thereof, in the range of 3 to 200 bases in length.) Consequently, preparation of a labelled oligonucleotide requires synthesis of an oligonucleotide bearing the aforementioned modifications. The oligomer is deprotected, liberating the nucleophile, which can react with a fluorescent label. This procedure entails at least a partial purification of the deprotected oligomer, reaction with the fluorescent dye derivative, removal of the excess reagent, and purification of the labelled oligomer. The purification of the product is often tedious and addition of the label increases synthesis time considerably. The overall process requires approximately two days, compared to less than one day for preparation of the unlabelled oligonucleotide.

Current procedures for the preparation of other types of non-radioactively labelled oligonucleotides usually require similar procedures.[5] In general, after deprotection and purification, the liberated nucleophile is coupled with a label (fluorescent, bioreactive, chemiluminescent, photolabile, etc.).

A few examples of labelling amidites, which enable direct attachment to the oligonucleotide, have been reported. An amidite bearing a chemically inert bathophenanthroline-ruthenium complex has been prepared and proposed as a fluorescent label for DNA sequencing and as a diagnostic probe.[6] Biotin-containing amidites have been prepared by several groups,[7,8] and Teoule and co-workers have prepared amidites with dinitrophenyl, dansyl, and pyrenyl labels.[8] Du Pont workers have also reported the synthesis of succinylxanthene-labelled amidites.[9] Cech and co-workers have published the synthesis of a fluorescein amidite where the linker side-arm is attached to one of the phenolic hydroxyls.[10]

Indocarbocyanine Dyes

Indocarbocyanines have long been known for their dye properties.[11] Recently some indocarbocyanine derivatives have proved to be extremely fluorescent and are quite useful in the labelling of biomolecules.[12,13a-d] Because of the low background fluorescence of biological materials in the longer wavelength portion of the spectrum, the signal-to-noise ratio of analyses using these dyes is very good.

It is usually advantageous to use as little of labelled probe as possible in order not to perturb the biological system or process with the probe. Therefore, the better the signal-to-noise ratio, the less probe is necessary. Indocarbocyanines have a very high absorbance and are among the "brightest" of the common dyes used in biological labelling.[14]

Indocarbocyanines have been introduced into proteins via carboxamide[13b,14] and thiourea[15] linkages. One method[12] of linking an indocarbocyanine to a nucleic acid used the introduction of an amino linker to the 5'-end of the oligonucleotide. An N-hydroxysuccinimide (NHS) ester of the indocarbocyanine carboxylic acid was added to an amino-linked oligonucleotide and the resulting conjugate isolated and purified. An alternative procedure would involve the addition of a linker phosphoramidite to the 5' end of an oligonucleotide on a DNA synthesizer. After deprotection and desalting of the phosphoramidite-linked oligonucleotide, the active nucleophile then reacts with the indocarbocyanine-carboxylic acid NHS ester to yield labelled oligonucleotide. The groups present in the linker are preferred because they are stable to conditions used in DNA synthesis, sequencing, and hybridization studies, as well as stability in long-term storage.

In spite of the long time for reaction and workup (compared to the synthesis of the oligonucleotide), generally introduction of labels has been done after deprotection of the oligonucleotide. Reaction and workup normally requires two days.

For these reasons, there is a need in the art of oligonucleotide labelling for an indocarbocyanine-linked phosphoramidite which allows the labelling of oligonucleotides in one step.

SUMMARY

One aspect of the present invention is directed to a chemical compound of the following formula where
R is one of H, trityl, 4-O-monomethoxytrityl, 4,4'-O-dimethoxytrityl, or acyl groups and R may be used as a protecting group or is an H;

R' is a phosphoramidite;

R" is one of H or lower alkyl groups;

R''' is one of H or lower alkyl groups;

$R^4$ is one of H, lower alkyl, acyl, or $(CH_2)_p COO(CH_2)_q CH_3$ where p is an integer from 0 to 4 and q is an integer from 0 to 4;

$R^5$ is one of H, lower alkyl, acyl, or $(CH_2)_p COO(CH_2)_q CH_3$ where p is an integer from 0 to 4 and q is an integer from 0 to 4;

n is an integer from 0 to 10;

m is an integer from 0 to 10;

r is 1, 2, or 3; and $X^-$ is a negative ion.

The most preferred version of the chemical compound is where R is 4-O-monomethoxytrityl; R' is N,N-diisopropyl-O-β-cyanoethyl phosphoramidite; R", R''', $R^4$, and $R^5$ are H; n is 1; m is 1; and r is 2.

Another preferred version of the chemical compound is where R is 4-O-monomethoxytrityl; R' is N,N-diisopropyt-O-β-cyanoethyl phosphoramidite; R", R''', $R^4$, and $R^5$ are H; n is 1; m is 1; and r is 1.

Another aspect of the present invention is directed to the compound described above, except that R is an aryl group-containing moiety, R' is an oligonucleotide and $R^4$ and $R^5$ are one of H, lower alkyl, acyl, and $(CH_2)_pCOOH$.

Another aspect of the present invention is a indocarbocyanine dye attached to a phosphoramidite. The dye comprises an indolinium ring and an indolenine ring in resonance connected by a carbon chain with conjugated double bonds. Each ring has a dimethyl substituent at the 3 position. The attachment of the dye to the amidite is through a linker at the nitrogen of either ring.

Another aspect of the present invention is directed to a method of attaching a fluorescent label to an oligonucleotide wherein the above compound serves as the fluorescent label.

Another aspect of the invention involves attaching a fluorescent label to an oligonucleotide by reacting the above compounds to the oligonucleotide such that the label becomes linked to the oligonucleotide at any point in the oligonucleotide chain. A preferred version of this aspect of the invention comprises linking a 5' end of the oligonucleotide to a phosphorus on the compound, oxidizing the linkage product, and removing the protecting group R from the oxidized linkage product. A preferred version of this inventive aspect comprises the presence of tetrazole and acetonitrile during the linkage reaction.

It is an object of the present invention to provide an indocarbocyanine dye in an amidite form.

It is another object of the present invention to provide a direct method of attaching an indocarbocyanine dye to an oligonucleotide.

It is an advantage of the present invention that an indocarbocyanine dye may be attached to an oligonucleotide in a one-step procedure.

These and other features, aspects, and advantages of the present invention will become better understood with regard to the following description, appended claims, and accompanying drawings.

DESCRIPTION OF THE INVENTION

Figure 1:
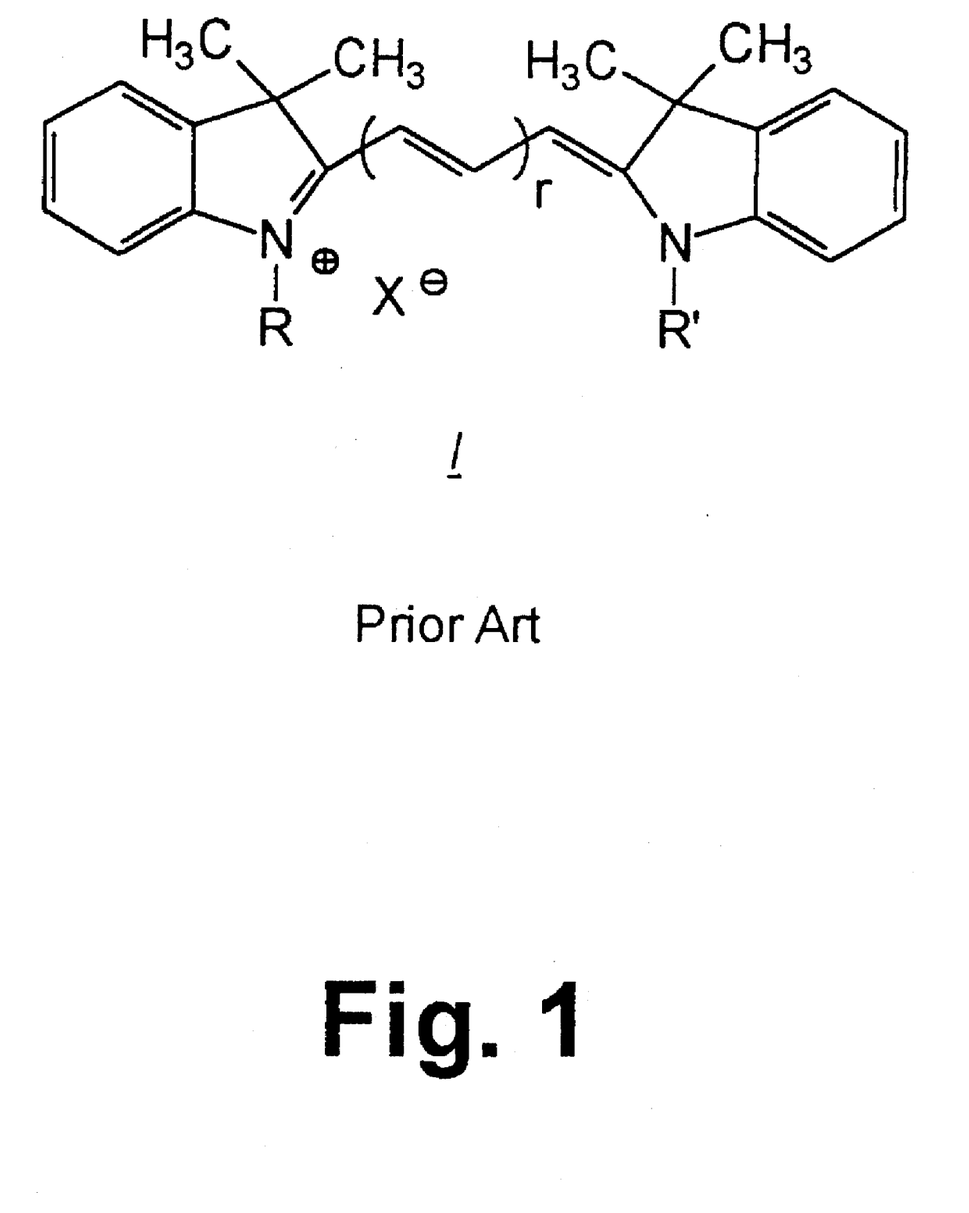
FIG. 1 shows the general structure of indocarbocyanine known in the prior art.

Indocarbocyanines have long been known for their dye properties.[11] Recently some indocarbocyanine derivatives have proved to be extremely fluorescent and are quite useful in the labelling of biomolecules.[12,13a-d] Indocarbocyanines of the general structure I (r=2) (in FIG. 1) fluoresce in the red region of the visible spectrum ($\lambda_{max}$ absorbance≅650 nm; $\lambda_{max}$ emission≅670 nm).[13b] When r=1, $\lambda_{max}$ absorbance≅552 nm; $\lambda_{max}$ emission≅570 nm.[13b] Because of the low background fluorescence of biological materials in the longer wavelength portion of the spectrum, the signal-to-noise ratio of analyses using these dyes is very good. It is advantageous to use as little as possible of labelled probes in order not to perturb the biological system or process with the probe. Therefore, the better the signal-to-noise ratio, the less probe is necessary. Indocarbocyanines have a very high absorbance ($\epsilon_{max}$≅215,000 for I (r=2), $\epsilon_{max}$≅130,000 for I (r=1)), an excellent fluorescent yield, and are among the "brightest" of the common dyes used in biological labelling.[14]

Figure 2:
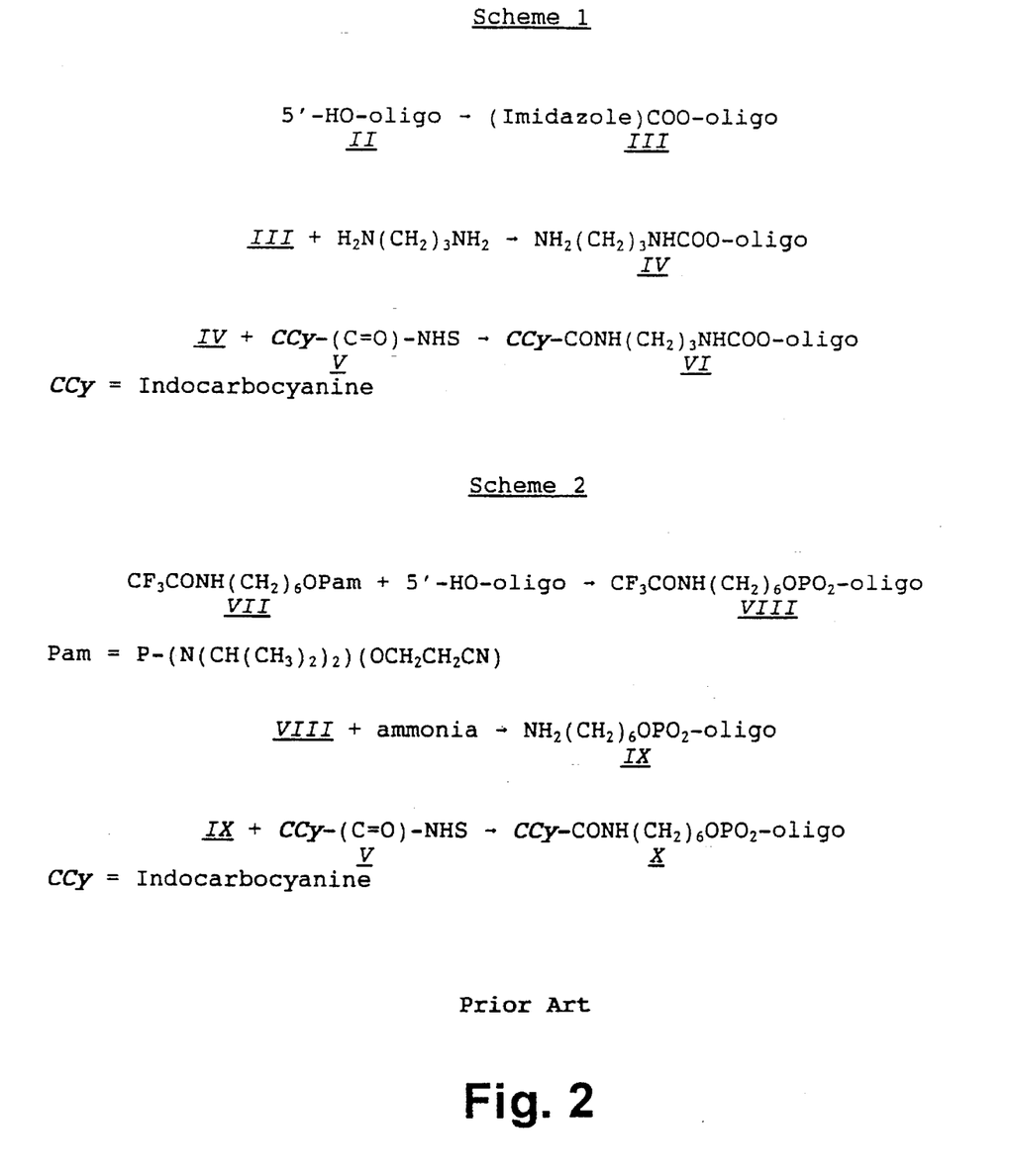
FIG. 2 shows prior art schemes for linking an indocarbocyanine to a nucleic acid.

One prior art method[12] of linking an indocarbocyanine to a nucleic acid used the introduction of an amino linker to the 5'-end of the oligonucleotide, as shown in Scheme 1 (in FIG. 2). An N-hydroxysuccinimide (NHS) ester of the indocarbocyanine carboxylic acid V was added to amino-linked oligo IV and the resulting conjugate VI isolated and purified.

An alternative prior art procedure (as shown in Scheme 2 in FIG. 2) could be the addition of a linker phosphoramidite, such as VII, to the 5'-end of an oligonucleotide on a DNA synthesizer. After deprotection and desalting of VIII, the active nucleophile in IX reacts with the indocarbocyanine-carboxylic acid NHS ester V to yield labelled oligonucleotide X. The groups present in the linker are preferred because they are stable to conditions used in DNA synthesis, sequencing, and hybridization studies, as well as stability in long-term storage. In spite of the long time for reaction and workup (compared to the synthesis of the oligonucleotide), introduction of indocarbocyanines has been done after deprotection of the oligonucleotide.

Figure 7:
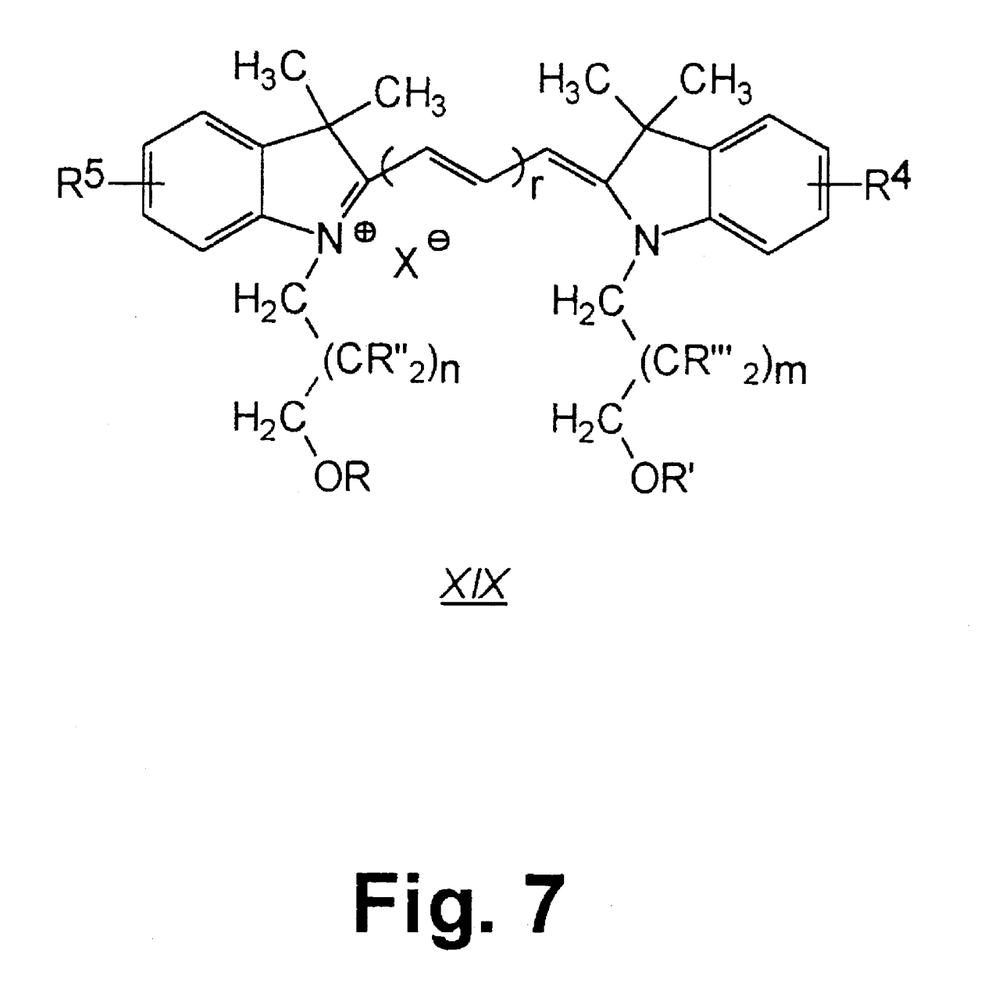
FIG. 7 shows the indocarbocyanine phosphoramidite of the present invention.

In order to facilitate the introduction of indocarbocyanine dye labels to oligonucleotides, we have synthesized novel phosphoramidites of several indocarbocyanine dyes, as shown by structure XIX in FIG. 7. The indocarbocyanine-linked phosphoramidite can be used directly on any DNA synthesizer to automatically add the dye to any nucleotide position, including the preferred 5'-end of the oligomer. The time for the coupling step (two minutes) and the concentration of reagent needed (0.1M) is the same as for the usual nucleoside phosphoramidites.[16] By the use of nucleoside protecting groups that are rapidly removed,[17] the total time for the preparation of a 20 base long labelled oligonucleotide is reduced from two days, as described above, to five hours. The yield of labelled product is also greater and the purification simpler than in the two-step method.

Consideration of the chemistry of oligonucleotides and indocarbocyanines was observed in the design of the invention. Since indocarbocyanines are generally unstable to basic conditions,[11] mild conditions for the rapid removal of protecting groups are necessary to deprotect an oligonucleotide bearing an indocarbocyanine moiety. Some nucleoside protecting groups can be removed under relatively mild conditions, especially the commercially available phenoxyacetyl protection,[17] making possible the improved method of attaching indocarbocyanines to oligonucleotides. The inclusion of an acid labile trityl group in the molecule allows the dye to be inserted anywhere in the oligonucleotide, or to have additional modifying groups present, such as a hydrophilic phosphate or a second dye moiety.

Figure 3:
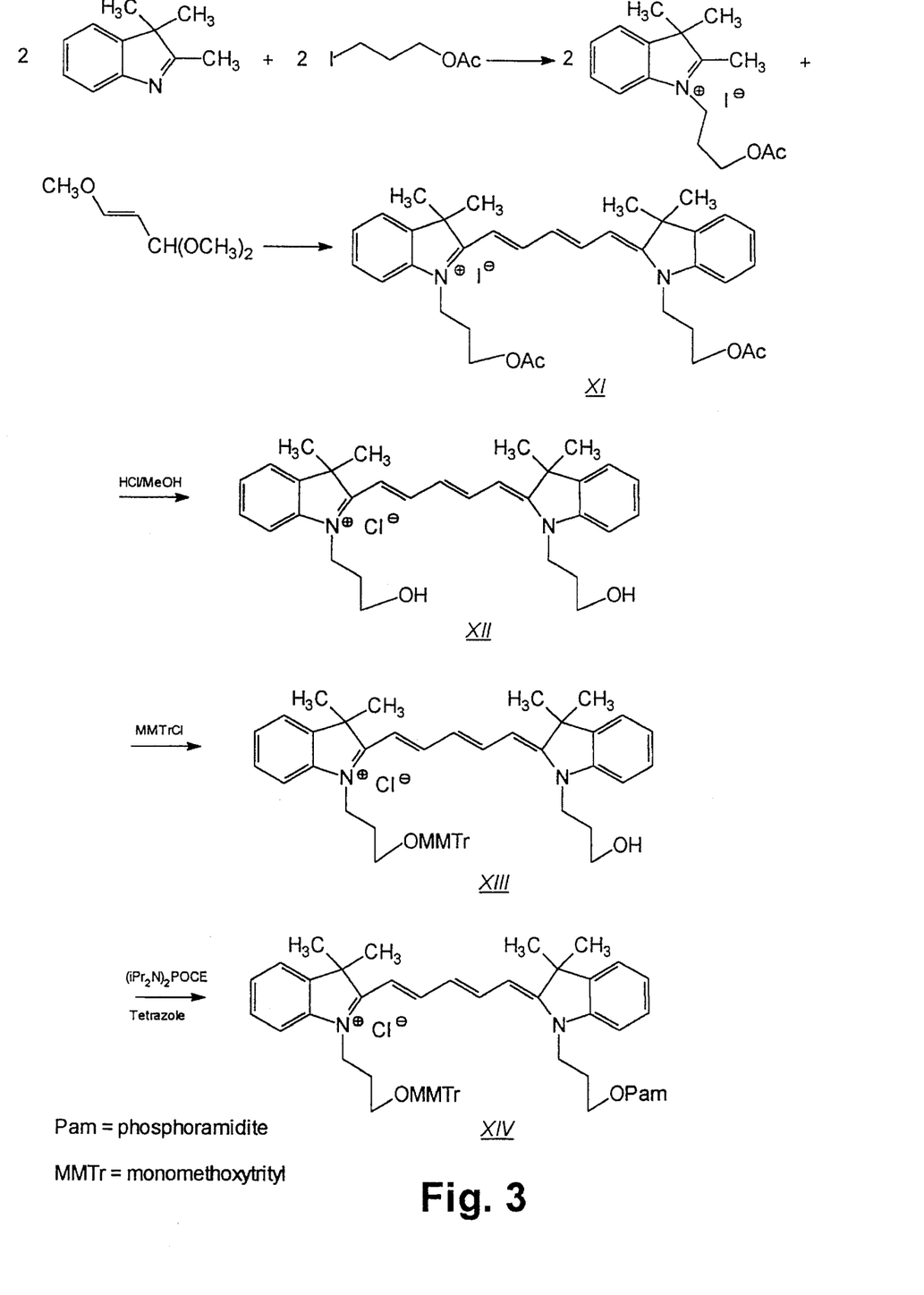
FIG. 3 shows a reaction scheme for the preparation of one version of the indocarbocyanine phosphoramidite of the present invention.

The general synthetic scheme for the preparation of a typical preferred indocarbocyanine phosphoramidite is shown in FIG. 3. The synthesis of the intermediate indocarbocyanine XI follows a modification of a standard literature method.[13b] If $R_4$ and $R_5$ are H, starting materials are readily commercially available. If $R_4$ or $R_5$ are not H, the starting materials are not commercially available. Methods to produce these compounds are generally known to those of skill in the art. For example, Southwick[13b] describes the preparation of modified indolenines. Suitable specific procedures are detailed below in the Examples.

Compounds XI and XII are symmetrical in their structures, since the double bond system resonates between the two nitrogens, leading to an averaging of the electron density throughout the chromophore. The preparation of a pure intermediate therefore is simpler for the preferred compound than if it were composed of dissimilar indolenines, which can result in cross-coupling and a mixture of products. However, the invention can be prepared with dissimilar indolenines if desired.

Figure 4:
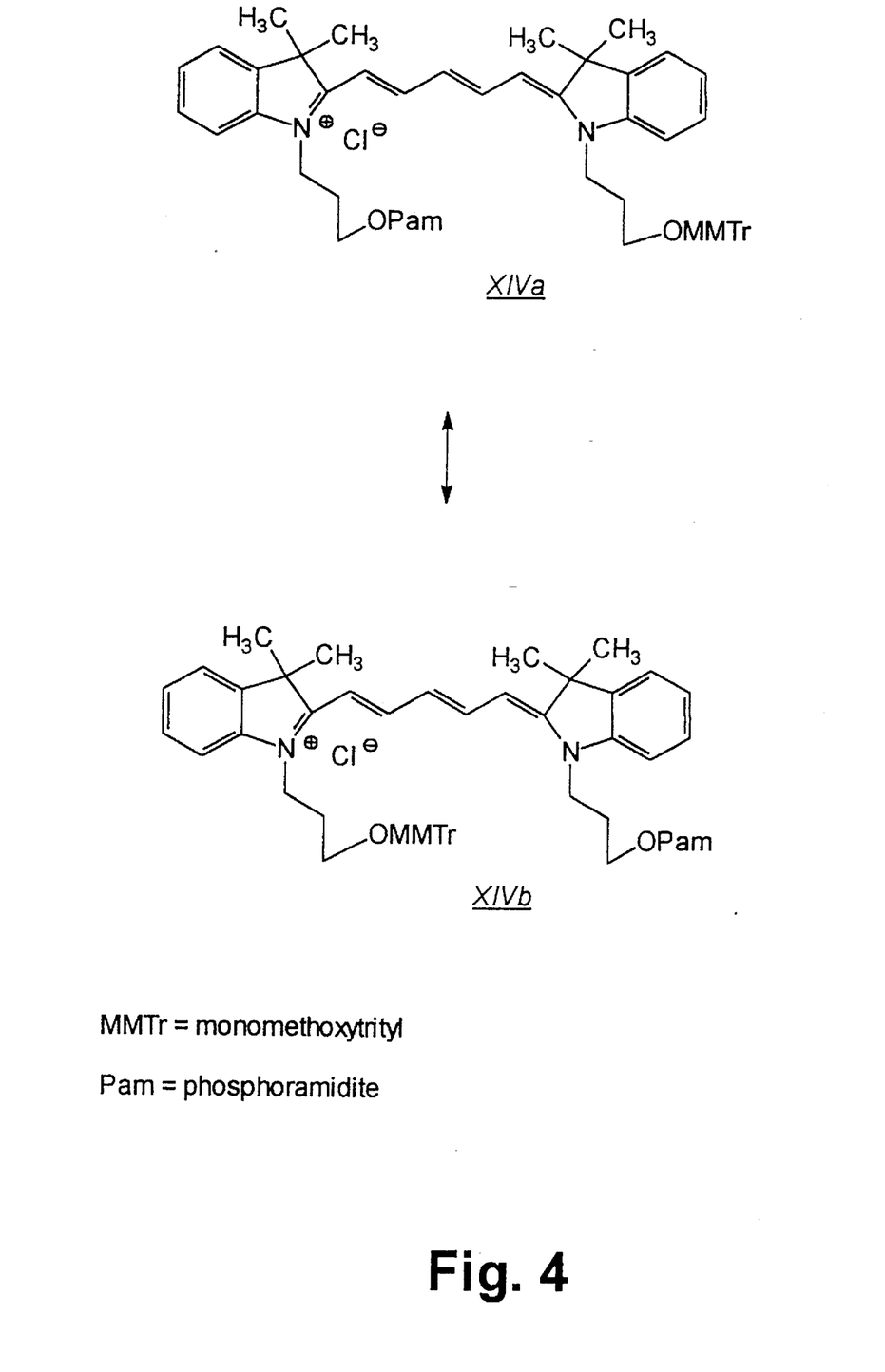
FIG. 4 shows the equivalence of tritylation in the version of indocarbocyanine phosphoramidite depicted in FIG. 3.

One novelty of the synthesis lies in the protection of one of the hydroxyls of compound XII, so that the other can be converted to the phosphoramidite (XIV). Since XII is symmetrical, it does not matter on which side the tritylation or acylation occurs. The ultimate phosphoramidites are identical, as shown in FIG. 4.

Neither the trityl nor phosphoramidite function has been introduced into indocarbocyanines previously. The amidite XIV has a visible spectrum characteristic of indocarbocyanines ($\lambda_{max}$ absorbance at 644 nm in dichloromethane).[13b] Labelled oligonucleotides prepared from XIV have $\lambda_{max}$ absorbance at 648 nm, the same $\lambda_{max}$ as labelled oligonucleotides prepared from the two step procedure outlined in Scheme 1, FIG. 2.[12]

Use of the various trityl groups, all of which are removable under acidic conditions, adds versatility to the invention. The monomethoxytrityl is preferred for its balance of stability during synthesis and ease of removal when desired. However, other protecting groups, such as dimethoxytrityl or acyl groups, are suitable for the present invention.

Figure 5:
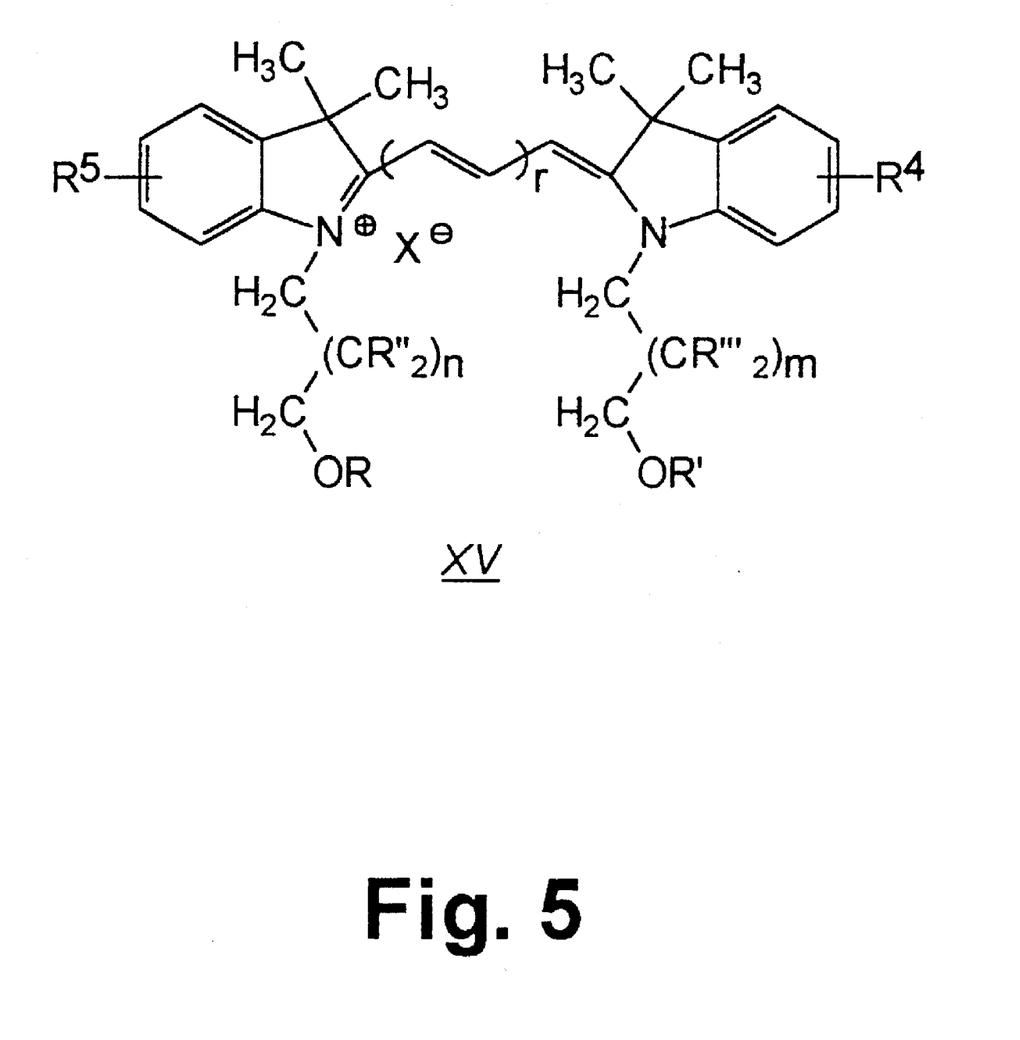
FIG. 5 shows a version of the indocarbocyanine phosphoramidite of the present invention after the reactions to add it to an oligonucleotide.

The dimethoxytrityl group is routinely removed by mild acid treatment in the cycle for synthesis of oligonucleotides with nucleoside phosphoramidites.[16] The indocarbocyanine moiety derived from the amidite can be treated as a nucleotide, in that it can be added anywhere in the sequence (R=oligonucleotide-5'-OH, R'=oligonucleotide-3'-OH, FIG. 5, XV), including the 3'-end (FIG. 5, XV, R=H, R'=oligonucleotide-3'-OH).

The preferred point of addition is the 5'-end of the oligonucleotide, where interference with hybridization by the dye label is minimized. Removal of the trityl group leaves a hydroxyl group (XVI, FIG. 6), which is the commonly used form. If it is desired to make the dye portion of the molecule more hydrophilic, a commercially available phosphorylating amidite can be used to introduce a phosphate group after detritylation of the (XVII, FIG. 6). At this point, a variety of aryl group-containing moieties may be added to the dye. By "aryl-group containing moieties" we mean groups that are capable of being added to the compound of the present invention at the R position after oligonucleotide coupling and should not interfere with the oligonucleotide. This moiety may have an advantageous effect on the fluorescence of the indocarbocyanine dye. An example, described in FIG. 6, is the addition of a second indocarbocyanine dye.

Figure 6:
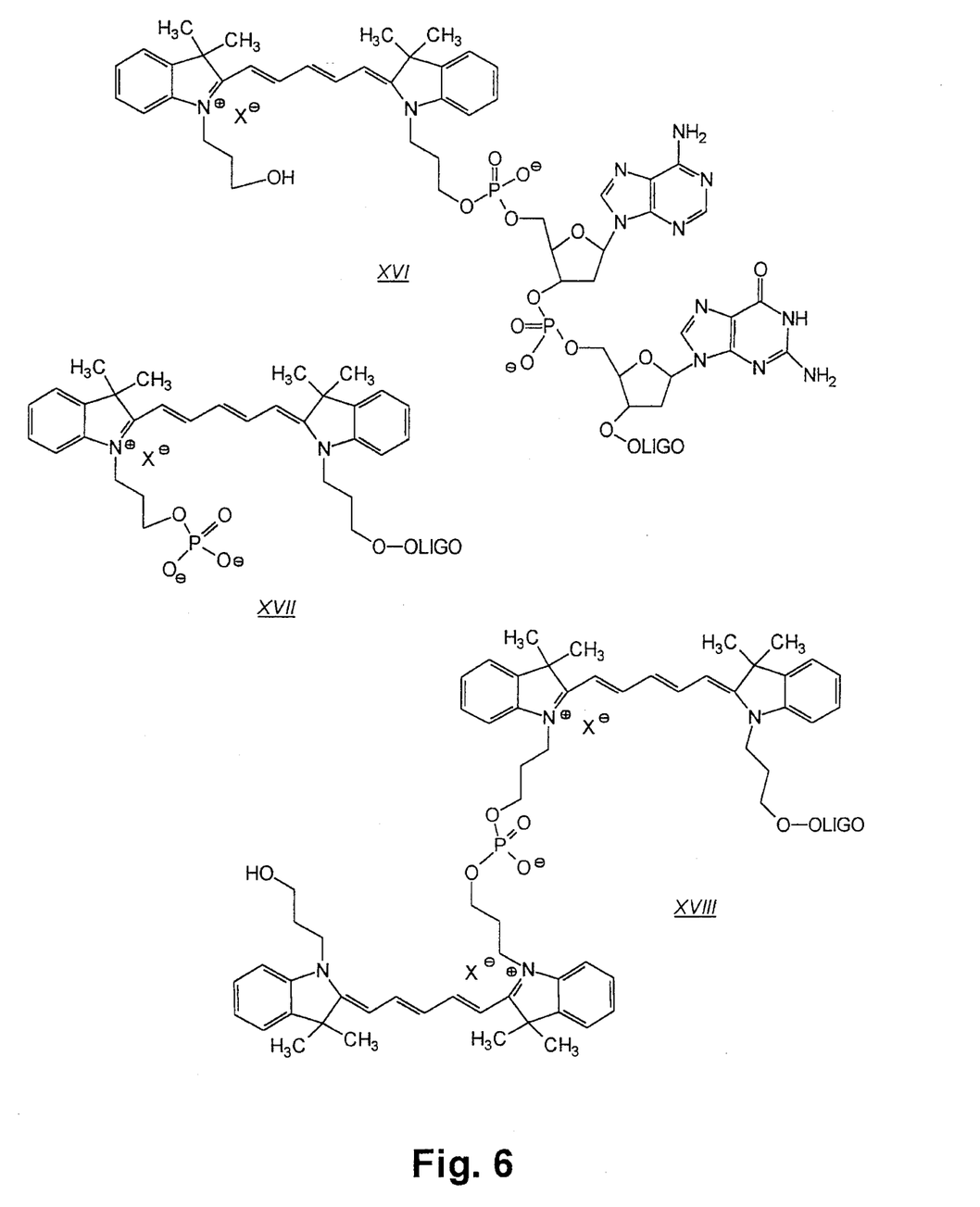
FIG. 6 shows various versions of the indocarbocyanine phosphoramidite of the present invention after linkage to oligonucleotides.

Addition of a second indocarbocyanine is possible by a second coupling of the dye-amidite (XVIII, FIG. 6). Also, other dyes which are available as amidites may be added in the same way to give a multi-color labelled oligonucleotide. Specific examples of suitable dyes are XIX where r=1 or 3 and R"—$R^5$=H and n=m=1; fluorescein; rhodamine; and acridine. Such multi-colored labelled oligonucleotides may be useful in multiple excitation and/or multiple detection mode instruments, or in detection by fluorescence resonance energy transfer.[18]

The synthesis of indocarbocyanine phosphoramidite XIX (FIG. 7), in which r=1, n=m=1, R=MMTr, and R'=β-cyanoethy-N,N-diisopropyl phosphoramidite, is accomplished by a single modification: the use of a one carbon unit instead of a three carbon unit in the condensation step.[13b] It is as versatile as XIV in its chemistry, but has a $\lambda_{max}$ absorbance at 552 nm and $\lambda_{max}$ emission at 570 nm. We envision that r may be either 1, 2, or 3.

One significance of this invention lies in the fact that indocarbocyanines, a useful label for fluorescent detection in biomolecules and of significance in DNA sequencing, can now be added to an oligonucleotide in a single automated step on any DNA synthesizer. The overall preparation and purification time to prepare dye-linked oligonucleotides is decreased from two days to 5 hours. Use of the indocarbocyanine amidite obviates the reaction of oligonucleotide and label after completion of the synthesis and deprotection. Furthermore it is not necessary to separate the product from a large excess of labelling reagent. Due to the liability of the indocarbocyanine moiety in concentrated ammonia at 55° C. for 5–16 hours, the use of phenoxyacetyl protection for the heterocyclic bases is recommended.

The compound of the present invention, as disclosed in compound XIX, possesses an $X^-$ moiety. $X^-$ indicates the presence of a negative ion. Preferably, this ion is a halide. Most preferably, it is a chloride ion.

EXAMPLES

All numbers in the following examples refer to the general structure XIX in FIG. 7, except as otherwise noted.

Example 1

(XIX, r=2, n=m=1, R=MMTr, R'=N,N-diisopropyl-O-β-cyanoethyl phosphoramidite, R"=R'"=$R^4$=$R^5$=H, same as XIV).

1-(3"-(1"-(β-Cyanoethyl-N,N-diisopropylphosphoramidite)propyl))-1'-(3'"-(1'"-(p-methoxytrityl)oxypropyl))-3,3,3',3'-tetramethyl-indodicarbocyanine chloride

3-Iodo-1-propyl acetate

3-Chloro-1-propyl acetate (45 mL, 50 g, 0.3661 mol, Aldrich) was added with stirring to 300 mL of anhydrous acetone, followed by 109.74 g (0.7322 mol., Baker) of NaI. The reaction was heated to reflux for a minimum of 17 hours. The acetone was evaporated and 300 mL of ether was added. The mixture was stirred, filtered, and the salts were washed with 200 mL of ether. The filtrate was extracted three times with water, dried with sodium sulfate, and the solvent evaporated. The residual oil was dried under vacuum overnight. Yield: 80–90% of 3-iodo-1-propyl acetate.

1-((3'-(1'-Acetoxypropyl))-2,3,3-trimethyl-(3H)-indolinium iodide

3-Iodo-1-propyl acetate (42 mL, 0.315 mol) was heated in a round bottom flask in an oil bath to 50° C. 2,3,3-Trimethyl-(3H)-indole (0.315 mol, 50.2 g, 52.3 mL, Kodak) was added and the temperature raised to 100° C. The mixture was heated at 100° C. for two to three hours, then cooled to room temperature. The gummy solid was dissolved in 250 mL 10% methanol/dichloromethane and 600 mL of ether was added. Crystallization took place overnight; the crystals were collected, washed with more ether, and dried in vacuo. Yield: 85–95% of 1-(1'-acetoxypropyl)-2,3,3-trimethyl-(3H)-indolinium iodide.

1,1'-Bis-(3''-(1''-hydroxypropyl))-3,3,3',3'-tetramethylindodicarbocyanine chloride (XII)

1-(1'-Acetoxypropyl)-2,3,3-trimethyl-(3H)-indolinium iodide (110 g, 0.284 mol) was dissolved in 800 mL dry acetonitrile with 24 mL (0.177 mol) of TEA and 8 mL (0.136 mol) of acetic acid in a round bottom flask in an oil bath heated to 100° C. In a dropping funnel, 1,3,3-trimethoxypropene (28.15 g. 0.45 mol, Kodak) was dissolved in 123 mL of dry acetonitrile. The mixture was added dropwise to the reaction flask over a period of one hour. The reaction was refluxed for 2 hours after the addition of the trimethoxypropene, during which time the progress was monitored by TLC and spectrophotometer readings. The starting material peak at 280 nm diminished as the product peak at 640 nm increased. When there was no change in the ratio of peak heights, the reaction mixture was cooled and evaporated to a gum.

The residue was dissolved in 3.2 L of 2M HCl in 50:50 water/methanol and stirred overnight at room temperature. The solvent was evaporated and the residue partitioned between dichloromethane and water. The organic layer was dried with sodium sulfate and the solvent evaporated. The residue was purified by column chromatography on silica gel using a mixture of 5/5/5/85 methanol:acetone:ethyl acetate:dichloromethane, followed by 8/8/8/76 of the same components. The appropriate fractions were pooled and evaporated to yield 60 g of 1,1'-bis-(3''-(1''-hydroxypropyl))-3,3,3',3'-tetramethyl-indodicarbocyanine chloride (XII). Purity of the product was monitored using HPLC (80% acetonitrile/20% 0.1M TEAA mobile phase, C18 column 4.6×250 mm, flow rate: 1 mL/min, detector: 640 nm). $^1$H NMR (CDCl$_3$): δ, 7.92, t, 2H, β-CH=; 7.4–7.17, m, 8H, aromatic; 7.01, t, 1H, γ-CH=; 6.51, d, 2H, α-CH=; 4.26, br t, 4H, 3'-CH$_2$; 3.85, br t, 4H, 1'-CH$_2$; 2.10, br m, 4H, 2'-CH$_2$; 1.70, s, 12H, CH$_3$. UV/visible spectrum: $\lambda_{max}$ 642 (598, sh.) nm; 324, 282, 248 nm.

1-(3'''-(1'''Hydroxypropyl))-1'-(3''-(1''-(p-methoxytrityl)oxypropyl))-3,3,3',3'-tetramethylindodicarbocyanine chloride (XIII)

Compound XII (6 g, 0.012 mol) was dried by co-evaporation three times with acetonitrile. It was dissolved in 65 mL of dry pyridine and 3.29 g (0.0108 mol) of monomethoxytrityl chloride (Aldrich) was added. The reaction was monitored by TLC and small increments of monomethoxytrityl chloride were added until the appearance of the bis-trityl compound began. The reaction was quenched by the addition of methanol and the mixture evaporated to dryness. The residue was purified on a silica gel column with 3/3/3/91 methanol:acetone:ethyl acetate:dichloromethane, followed by 5/5/5/85 as the eluent. The unreacted dihydroxy compound was recovered by stripping the column with 50/50 methanol:dichloromethane. Yield of compound XIII was 3–4 g. Purity was determined by HPLC (90% acetonitrile/10% 0.1M TEAA mobile phase, C3 column 4×60 mm, flow rate: 1 mL/min, detector: 640 nm). The purified compound could be crystallized from acetonitrile (mp 172°–175° C. dec.). $^1$H NMR (CDCl$_3$): δ, 8.12, t, 1H, β or β'-CH=; 8.00, t, 1H, β or β''-CH=; 7.44–7.05, m, 18H, aromatic; 6.82, d, 2H, aromatic; 6.41, t, 1H, γ-CH=; 6.32, br d, 1H, α or α'-CH=; 6.18, d, 1H, α or α''-CH=; 4.36, t, 2H, 3'' or 3'''-CH$_2$; 4.18, t, 2H, 3'' or 3'''-CH$_2$; 3.86, q, 2H, 1'''-CH$_2$OH; 3.80, s, 3H, OCH$_3$; 3.43, br, 1H, OH; 3.11, t, 2H, 1''-CH$_2$OMMTr; 2.11, br m, 4H, 2'', 2'''-CH$_2$; 1.70, s, 6H, CH$_3$; 1.68, s, 6H, CH$_3$. UV/visible spectrum (dichloromethane): $\lambda_{max}$=644 nm (600 sh.); 370, 324, 244 nm.

1-(3''-(1''-(β-Cyanoethyl-N,N-diisopropylphosphoramidite)propyl))-1'-(3'''-(1'''-(p-methoxytrityl)oxypropyl))-3,3,3',3'-tetramethylindodicarbocyanine chloride (XIV)

Compound XIII (4.0 g, 0.0051 mol) was dried by co-evaporation with dry acetonitrile, followed by dissolution in 33 mL of dry acetonitrile. A few grains of tetrazole were added to the solution, followed by the phosphitylating agent, bis-(N,N-diisopropyl)-β-cyanoethyl phosphordiamidite,[19] (2.32 g, 0.0077 mol). The reaction was monitored by TLC until the starting material was consumed. The solvent was evaporated and the flask evacuated under high vacuum for two hours. The resulting solid was triturated with dry ether at least five times, until the color of the ether was no longer green. The solid was then dried under high vacuum overnight and stored under argon at −20° C. Yield of compound XIV: approximately 4.0 g, purity by HPLC (C3 column, 90% acetonitrile/0.1M triethylammonium acetate), approximately 95%, monitored at 644 nm. $^1$H NMR (CDCl$_3$): δ, 8.35, dt, 2H, β, β'—CH=; 7.47–7.05, m, 18H, aromatic; 6.82, d, 2H, aromatic; 6.40, t, 1H, γ-CH=; 6.25, 6.18, dd, 1H, α, α'-CH=; 4.24, br m, 4H, 3'', 3'''-CH$_2$; 3.95–3.55, m, 6H, 1''-CH$_2$,isopropyl-CH, OCH$_2$CH$_2$CN; 3.78, s, 3H, OCH$_3$; 3.10, br t, 2H, CH$_2$OMMTr; 2.64, t, 2H, CH$_2$CN; 2.12, br m, 4H, 2'', 2'''-CH$_2$; 1.82, 1.71, ds, 12H, CH$_3$; 1.22, dd, 12H, isopropyl CH$_3$. $^{31}$P NMR (CDCl$_3$+0.1% ethyldiisopropylamine, trimethyl phosphate standard ) δ, 145.68 (purity~91%). UV/visible spectrum (dichloromethane): $\lambda_{max}$ 644 nm (600 sh.); 324, 282, 244 nm.

Example 2

(XIX, r=1, n=m=1, R=MMTr, R'=N,N-diisopropyl-O-β-cyanoethyl phosphoramidite, R''=R'''=R$^4$=R$^5$=H)

1-(3''-(1''-(β-Cyanoethyl-N,N-diisopropylphosphoramidite)propyl))-1'-(3'''-(1'''-(p-methoxytrityl)oxypropyl))-3,3,3',3'-tetramethyl-indocarbocyanine chloride

1,1'-Bis-(3''-(1''-hydroxypropyl))-3,3,3',3'-tetramethylindocarbocyanine chloride (XIX, r=1, n=m=1, R=R'=R''=R'''=R$^4$=R$^5$=H)

1-(1'-Acetoxypropyl)-2,3,3-trimethyl-(3H)-indolinium iodide (5 g, 0.013 mol) was dissolved in 60 mL of pyridine and triethylorthoformate (0.038 mol, Aldrich) was added. The reaction mixture was refluxed for 1.5 hr, cooled, and evaporated. The residue was dissolved in 73 mL of 4M HCl mixed with 73 mL of methanol. The reaction was stirred overnight at ambient temperature. Some crystals which had formed were filtered and the filtrate evaporated to dryness. The residue was purified on a silica gel column with 5:5:5:85 methanol/ethyl acetate/acetone/dichloromethane, followed by 8:8:8:76 of the same. The pure fractions and the crystals were combined. HPLC: C18 column, 80% acetonitrile/0.1M triethylammonium acetate); UV/visible spectrum (80% acetonitrile/0.1 M triethylammonium acetate, pH 7): $\lambda_{max}$ 545 nm (513 sh.); 280 nm. $^1$H NMR (CDCl$_3$): δ, 8.35, t, 1H, β-CH=; 7.38–7.14, m, 8H, aromatic; 6.84, d, 2H, α, α'-CH=; 4.75, t, 4H, 3, 3'-CH$_2$; 3.93, t, 2H, OH; 3.77, q, 4H, 1,1'-CH$_2$; 2.07, m, 4H, 2, 2'-CH$_2$; 1.68, s, 12H, CH$_3$.

1-(3'''-(1'''-Hydroxypropyl))-1'-(3—(1''-
(p-methoxytrityl)oxypropyl))-3,3,3',3'-
tetramethylindocarbocyanine chloride (XIX, r=1,
n=m=1, R=MMTr, R'=R''=R'''=R$^4$=R$^5$=H)

This compound was prepared in a procedure identical to that of compound XIII.

1-(3''-(1''-(β-Cyanoethyl-N,
N-diisopropylphosphoramidite)propyl))-1'-(3'''-(1'''-
(p-methoxytrityl)oxypropyl-3,3,3',3'-
tetramethyl-indocarbocyanine chloride [XIX,
r=1,n=m=1, R=MMTr,
R'=N,N-diisopropyl-O-β-cyanoethyl
phosphoramidite, R''=R'''=R$^4$=R$^5$=H;

This compound was prepared in a procedure identical to that of compound XIV. HPLC: C3 column, 90% acetonitrile/0.1M triethylammonium acetate; UV/visible spectrum (dichloromethane): $\lambda_{max}$ 556 nm (522 sh.); 282, 248, 232 nm. $^1$H NMR (CDCl$_3$): δ, 8.35, t, 1H, β-CH=; 7.45–7.00, m, 10H, aromatic+α, α'-CH=; 6.78, d, 2H, aromatic; 4.41, 4.30, 2t, 4H, 3, 3'-CH$_2$; 3.96–3.40, m, 6H, 1''-CH$_2$, isopropyl-CH, OCH$_2$CH$_2$CN; 3.75, s, 3H, OCH$_3$; 3.10, br t, 2H, C H$_2$OMMTr; 2.64, t, 2H, CH$_2$CN; 2.29, 2.17, 2m, 4H, 2'', 2'''-CH$_2$; 1.70, 163, ds, 12H, CH3; 1.22, d, 12H, isopropyl CH$_3$.

Example 3

(XIX, r=2, n=m=4, R=MMTr, R'=N,N-diisopropyl-O-β-cyanoethyl phosphoramidite, R''=R'''=R$^4$=R$^5$=H)

1 -(6''-(1''-(β-Cyanoethyl-N,N-
diisopropylphosphoramidite)hexyl))-1'-
(6'''-(1'''-(p-methoxytrityl)oxyhexyl))-3,3,3',3'-
tetramethyl-indodicarbocyanine chloride In a method completely analogous to the preparation of Example 1, the compound named in Example 3 was prepared. The only difference was that 6-chlorohexyl acetate (Aldrich) was used instead of 3-chloropropyl acetate.

Example 4

(XIX, r=2, n=m=1, R=DMTr, R'=N,N-diisopropyl-O-β-cyanoethyl phosphoramidite, R''=R'''=R$^4$=R$^5$=H)

1-(3''-(1''-(β-Cyanoethyl-N,N-
diisopropylphosphoramidite)propyl))-1'-
(3'''-(1'''-(p,p'-dimethoxytrityl)oxypropyl))-3,3,3',3'-
tetramethyl-indodicarbocyanine chloride In a method completely analogous to the preparation of Example 1, the compound named in Example 4 was prepared. The only difference was that dimethoxytrityl chloride (Chem Impex) was used instead of monomethoxytrityl chloride.

Example 5

(XIX, r=2, n=m=1, R=pivaloyl, R'=N,N-diisopropyl-O-β-cyanoethyl phosphoramidite, R''=R'''=R$^4$=R$^5$=H)

1-(3''-(1''-(β-Cyanoethyl-N,N-
diisopropylphosphoramidite)propyl))-
1'-(3'''-(1'''-(pivaloyloxypropyl))-3,3,3',3'-
tetramethyl-indodicarbocyanine chloride 1-(3'''-(1'''-Hydroxypropyl))-1'-
(3''-(1''-pivaloyloxypropyl))-3,3,3',3'-
tetramethyl-indodicarbocyanine chloride Compound XII (1 g, 0.002 mol) was dissolved in 16 mL of dry pyridine and 0.182 mL (0.0015 mol) of pivaloyl chloride (Aldrich) was added. After five minutes the pyridine was evaporated and the residue was freed from residual pyridine by two co-evaporations each with toluene and dichloromethane. The product was purified by column chromatography on flash grade silica using 3:3:3:91 methanol/acetone/ethyl acetate/dichloromethane as the eluent. The appropriate fractions were carefully separated from the contaminating bis-pivaloyl compound. Yield: 0.15 g (10%). Purity=99+% by HPLC (90% acetonitrile/10% 0.1M TEAA mobile phase, C18 column 4.6×250 mm, flow rate: 1 mL/min, detector: 640 nm). UV/visible spectrum: $\lambda_{max}$ 640 (604, sh.) nm. $^1$H NMR (CDCl$_3$): δ, 8.02, t, 1H, β or β'-CH=; 7.92, t, 1H, β or β'-CH=; 7.43–6.96, m, 8H, aromatic; 6.82, d, 2H, aromatic; 6.95, t, 1H, γ-CH=; 6.64, br d, 1H, α or α'-CH=; 6.27, d, 1H, α or α'-CH=; 4.38, t, 2H, 3'' or 3'''-CH$_2$; 4.20, t, 2H, 3'' or 3'''-CH$_2$; 4.11, t, 2H, 1''-CH/OPiv; 3.88, q, 2H, 1'''-CH$_2$OOH; 3.42, t, 1H, OH; 2.15, br m, 4H, 2'', 2'''-CH$_2$; 1.74, d, 12H, CH$_3$; 1.29, s, 9H, Pivaloyl CH$_3$.

1-(3''-(1''-β-Cyanoethyl-N,N-
diisopropylphosphoramidite)propyl))-1'-(3'''-1'''-
(pivaloyloxypropyl)-3,3,3',3'-tetramethyl-
indodicarbocyanine chloride The pivaloyl derivative of XII (95 mg, 0.00016 mol) was dissolved in 0.8 mL of dry dichloromethane and one crystal of tetrazole was added. The phosphitylating agent, bis-(N,N-diisopropyl)-β cyanoethyl phosphordimidite (96.8 mg, 0.00032 mol) was added and the reaction proceeded for 15 minutes. TLC analysis showed the conversion to the amidite to be almost quantitative. The reaction was evaporated to dryness and the residual solvent removed by evacuation under high vacuum. Excess phosphitylating reagent was removed by extraction with dry ether. The product was used without further purification to prepare a labelled oligonucleotide.

Example 6

Synthesis of an indodicarbocyanine labelled oligonucleotide.

Compound XIV (100 mg) was dissolved in 1 mL of dry acetonitrile (0.1M solution) and placed on an automated DNA synthesizer (Gene Assembler Plus®, Pharmacia LKB Biotechnology). After the synthesis of the 17 mer oligonucleotide using PAC protected nucleoside phosphoramidites (Pharmacia LKB Biotechnology), following the procedure suggested by the manufacturer, 50 µL of the solution of XIV was delivered to the reaction column with. 100 µL of a 0.5M tetrazole activator solution. The mixture was cycled over the support containing the 5'-OH oligonucleotide for two minutes. Following the removal of excess XIV, the typical coupling cycle was completed by oxidation, capping, and detritylation.[16]

The indodicarbocyanine-labelled oligonucleotide was deprotected in concentrated ammonia for 20 minutes at 60° C. The ammonia solution was desalted by gel filtration (NAP-10, Pharmacia LKB Biotechnology) and the product isolated by reverse phase HPLC: gradient of 10–40% A in B over 30 minutes; A=acetonitrile, B=0.1M triethylammonium acetate, pH 7. Retention time ~15–20 minutes, depending on the length of the oligonucleotide. Gel electrophoresis: On an 18% polyacrylamide gel, the labelled oligonucleotide ran as a sharp band approximately 3 or 4 bases longer than the unlabelled oligo. The blue color of the dye was visible in the gel. UV/visible spectrum: $\lambda_{max}$ 648 (604, sh.) nm; 260 nm; $A_{260}/A_{648}$=0.823.

Example 7

Synthesis of a bis-indodicarbocyanine-labelled oligonucleotide

The compound named was synthesized as in Example 6, except that after the completion of the cycle adding the first indodicarbocyanine (including detritylation), a second indodicarbocyanine moiety was added. Deprotection and isolation were done in a manner analogous to that in Example 6. HPLC UV/visible spectrum: $\lambda_{max}$648 (604, sh.) nm; 260 nm Example 8

Synthesis of a phosphoryl-indodicarbocyanine-labelled oligonucleotide

The compound named was synthesized as in Example 6, except that after the completion of the cycle adding the first indodicarbocyanine (including detritylation), an amidite which yields a phosphate group on deprotection was added. Deprotection and isolation were both done in a manner analogous to that in Example 6. HPLC: C18 column, 10%–40% acetonitrile/0.1M triethylammonium acetate over 30 minutes; UV/visible spectrum: $\lambda_{max}$648 (604, sh.) nm; 260 nm

Although the present invention has been described in considerable detail with reference to certain preferred versions thereof, other versions are possible. For example, where $R_4$ and $R_5$ are $CH_2COOR$ and where R is an alkyl or COOR or $CH_2OP=O$ (O-cyanoethyl)$_2$.

Therefore, the spirit and scope of the appended claims should not be limited to the description of the preferred versions contained herein.

1. Brumbaugh, J. A.; Middendorf, L.R.; Grone, D. L.; Ruth, J. R., *Proc. Nat. Acad. Sci. U.S.A.* 1988, 85, 5610–5614.
2. Kaiser, R. J.; MacKellar, S. L.; Vinayak, R. S.; Sanders, J. Z.; Saavedra, R. A.; Hood, L. E.; *Nuc. Acids Res.* 1989, 17, 6087–6102.
3. Coull, J. M.; Weith, H. L.; Bischoff, R.; *Tetrahedron Lett.* 1986, 27, 3991–3994.
4. Ansorge, W.; Sproat, B. S.; Stegemann, J.; Schwager, C., *J. Biochem. Biophys. Methods* 1986, 13, 315–323.
5. (a) pochet, S.; Huynh-Dinh, T.; igolen, J. *Tetrahedron* 1988, 43, 3481. (b) Haralambidis, J.; et al., *Tetrahedron Lett.* 1987, 28, 5199. (c) Urdea, M. S.; Warner, B. D., Running, J. A.; Stempien, M.; Clyne, J.; Horn, T. *Nuc. Acids Res.* 1988, 16, 4937. (d) Le Brun, S.; Duchange, N.; Namane, A.; Zakin, M. M.; Huynh-Dinh, T.; Igolen, J. *Biochemie* 1989, 71, 319.
6. Bannwarth, W.; Schmidt, D. *Tetrahedron Lett.* 1989, 30, 1513–1516.
7. Alves, A. M.; Holland, D.; Edge, M. D. *Tetrahedron Lett.* 1989, 30, 3089–3092.
8. Roget, A.; Bazin, H.; Teoule, R. *Nuc. Acids Res.* 1989, 17, 7643–7651.
9. Trainor, G. L.; Cocuzza, A. J.; Hobbs, F. W.; Johnson, P. R.; Emmett, G. E.; Zagursky, R. J.; Livak, K. J.; Korolkoff, P. N.; Jensen, M. A. (Poster at Cold Spring Harbor Conference, April, 1989, entitled "Chemical Reagents for Molecular Biology").
10. Schubert, F.; Ahlert, K.; Cech, D.; Rosenthal, A. *Nuc. Acids Res.* 1990, 18, 3427.
11. For a general reference, see *The Cyanine Dyes and Related Compounds*, Frances M. Hamer, Interscience, New York, 1964, Ch. 7.
12. Yu. H.; Ernst, L.; Wagner, M.; Waggoner, A. *Nuc. Acids Res.* 1992, 20, 83–88.
13. (a) U.S. Pat. No. 4,981,977, Southwick, P. L.; Waggoner, A. S. (b) Southwick, P. L.; Ernst, L. A.; Tauriello, E. W.; parker, S. R.; Mujumdar, R. B.; Mujumdar, S. R.; Clever, H. A.; Waggoner, A. S. *Cytometry,* 1990, 11, 418–430. (c) Patonay, G.; Antoine, M. D., *Anal. Chem.,* 1991, 63, 321A–326A. (d) Galbraith, W.; Wagner, M. C. E.; Chao, J.; Abaza, M.; Ernst, L. A.; Nederlof, M. A.; Hartsock, R. J.; Taylor, D. L.; Waggoner, A.S., *Cytometry,* 1991, 12, 579–596.
14. Wessendorf, M. W.; Brelje, T. C., *Histochemistry,* 1992, 98, 81–85.
15. Ernst, L. A.; Gupta, R. K.; Mujumdar, R. B.; Waggoner, A. S., *Cytometry,* 1989, 10, 3–10.
16. Pharmacia LKB Biotechnology Gene Assembler Plus® Manual.
17. Schulhof, J. C.; Molko, D.; Teoule, R., *Nuc. Acids Res.,* 1987, 15, 397–316. (Available from Pharmacia LKB Biotechnology and several others.)
18. Agrawal, S.; Zamecnik, P.C., *Nuc. Acids Res.,* 1990, 18, 5419–5423.
19. Gaffney, B.; Jones, R. A., *Biochemistry,* 1989, 28, 5882.

We claim:

1. A chemical compound of the following formula:

wherein:

R is selected from the group consisting of H, trityl, 4-O-monomethoxytrityl, 4,4'-O-dimethoxytrityl, and acyl groups, and whereby R can be used as a protecting group or is an H;

R' is a phosphoramidite;

R" is selected from the group consisting of H and lower alkyl groups;

R''' is selected from the group consisting of H and lower alkyl groups;

$R^4$ is selected from the group consisting of H, lower alkyl, acyl, and $(CH_2)_pCOO(CH_2)_qCH_3$ wherein p is an integer from 0 to 4 and q is an integer from 0 to 4;

$R^5$ is selected from the group consisting of H, lower alkyl, acyl, and $(CH_2)_pCOO(CH_2)_qCH_3$ wherein p is an integer from 0 to 4 and q is an integer from 0 to 4;

n is an integer from 0 to 10;

m is an integer from 0 to 10;

r is 1, 2, or 3; and $X^-$ is a negative ion.

2. The chemical compound of claim 1 wherein:

R is 4-O-monomethoxytrityl;

R' is N,N-diisopropyl-O-β-cyanoethyl phosphoramidite;

R", R'", $R^4$, and $R^5$ are H;

n is 1;

m is 1; and r is 2.

3. The chemical compound of claim 1 wherein:

R is 4-O-monomethoxytrityl;

R' is N,N-diisopropyl-O-β-cyanoethyl phosphoramidite;

R", R'", $R^4$, and $R^5$ are H;

n is 1;

m is 1; and r is 1.

4. The chemical compound of claim 1 wherein:

R is pivaloyl;

R' is N,N-diisopropyl-O-β-cyanoethyl phosphoramidite;

R", R'", $R^4$, and $R^5$ are H;

n is 1;

m is 1; and r is 2.

5. The chemical compound of claim 1 wherein:

R is 4,4'-O-dimethoxytrityl;

R' is N,N-diisopropyl-O-β-cyanoethyl phosphoramidite;

R", R'", $R^4$, and $R^5$ are H;

n is 1;

m is 1; and r is 2.

6. The chemical compound of claim 1 wherein:

R is 4-O-monomethoxytrityl;

R' is N,N-diisopropyl-O-β-cyanoethyl phosphoramidite;

R", R'", $R^4$, and $R^5$ are H;

n is 4;

m is 4; and r is 2.

7. A chemical compound of the following formula:

wherein:

R is selected from the group consisting of aryl-group-containing moieties, wherein said moieties do not interfere with the attachment of an oligonucleotide at the R' position;

R' is an oligonucleotide;

R" is selected from the group consisting of H and lower alkyl groups;

R'" is selected from the group consisting of H and lower alkyl groups;

$R^4$ is selected from the group consisting of H, lower alkyl, acyl, and $(CH_2)_pCOOH$ wherein p is an integer from 0 to 4;

$R^5$ is selected from the group consisting of H, lower alkyl, acyl, and $(CH_2)_pCOOH$ wherein p is an integer from 0 to 4;

n is an integer from 0 to 10;

m is an integer from 0 to 10; and r is 1, 2, or 3; and $X^-$ is a negative ion.

8. An indocarbocyanine dye attached to a phosphoramidite, said dye comprises an indolinium ring and an indolinine ring in resonance wherein said rings are connected by a carbon chain with conjugated double bonds, wherein said rings each have a dimethyl substituent at the 3 position, wherein said phosphoramidite is attached through a first linker at the nitrogen of either ring, wherein a protecting group is attached through a second linker at the nitrogen of the other ring, and wherein no glyceryl linker is interposed between a) said protecting group and said phosphoramidite and b) said indocarbocyanine dye.

9. A method of linking a fluorescent label to an oligonucleotide, comprising:

reacting the compound of claim 1 with said oligonucleotide such that said label becomes linked to said oligonucleotide.

10. The method of claim 9 wherein the reacting step comprises linking the 5' end of the oligonucleotide to a phosphorus on said compound, oxidizing the resulting linked digonucleotide and compound, and removing any protecting group from the oxidized linked oligonucleotide and compound.

11. The method of claim 10 wherein said linking is done in the presence of tetrazole and acetonitrile.

* * * * *